United States Patent [19]

Shaw

[11] Patent Number: 5,907,064
[45] Date of Patent: May 25, 1999

[54] PROCESS FOR PRODUCING ORGANIC TRISULFIDES

[75] Inventor: James E. Shaw, Bartlesville, Okla.

[73] Assignee: Phillips Petroleum Co., Bartlesville, Okla.

[21] Appl. No.: 09/081,111

[22] Filed: May 19, 1998

[51] Int. Cl.⁶ .................................................. C07C 321/12
[52] U.S. Cl. ................................................. 568/21; 568/25
[58] Field of Search .................................. 568/21, 24, 25

[56] References Cited

U.S. PATENT DOCUMENTS

| | | | |
|---|---|---|---|
| 4,827,040 | 5/1989 | Labat | 568/21 |
| 5,068,445 | 11/1991 | Arretz | 568/21 |
| 5,232,623 | 8/1993 | Shaw | 252/183.13 |
| 5,442,123 | 8/1995 | Arretz | 568/26 |
| 5,530,163 | 6/1996 | Shaw | 568/26 |
| 5,565,517 | 10/1996 | Efner | 524/714 |
| 5,679,626 | 10/1997 | Born | |

*Primary Examiner*—Gary Geist
*Assistant Examiner*—Jean F. Vollano
*Attorney, Agent, or Firm*—Lucas K. Shay

[57] ABSTRACT

A process for producing an organic trisulfide compound comprises contacting, in the presence of a catalyst, a mercaptan with an organic polysulfide compound to produce a product mixture and optionally contacting the product mixture with an acid wherein the catalyst comprises a base and surfactant and the organic polysulfide contains about 4 or more sulfur atoms per molecule.

19 Claims, No Drawings

5,907,064

PROCESS FOR PRODUCING ORGANIC TRISULFIDES

The present invention relates to a process for producing an organic trisulfide compound.

BACKGROUND OF THE INVENTION

Organic polysulfides such as alkyltrisulfides are useful for many purposes such as additive for elastomers, as antioxidants for lubricating oils, as intermediate for the production of organic chemicals, insecticides, and germicides and as additive to diesel fuels to improve the cetane number and ignition qualities of these fuels. These compounds are also useful in the compounding of extreme pressure lubricants and in the acceleration of rubber treating processes.

Such trisulfide compounds can be produced by reacting mercaptans with elemental sulfur in the presence of a basic catalyst. For example, Shaw (U.S. Pat. No. 5,530,163) discloses that organic trisulfides can be produced from a mercaptan and sulfur catalyzed by a basic catalyst. However, there is always a need to develop an improved process to produce an organic trisulfide compound for industrial uses.

SUMMARY OF THE INVENTION

An object of the present invention is to provide a process for producing an organic trisulfide. Also an object of the present invention is to convert a polysulfide containing more than 3 sulfur atoms per molecule to trisulfide. Another object of the present invention is to reduce the odor associated with the organic trisulfide compound. A further object of the present invention is to produce an organic trisulfide that is stable and deodorized. An advantage of the present invention is the reduction of the concentration of sulfur content of an organic polysulfide compound containing more than three sulfur atoms per molecule. Other objects and advantages will become more apparent as the invention is more fully disclosed hereinbelow.

According to the present invention, a process for producing an organic trisulfide is provided which comprises contacting a mercaptan with an organic polysulfide compound having about 4 or more sulfur atoms per polysulfide molecule in the presence of a catalyst wherein the catalyst comprises a base and optionally a surfactant.

DETAILED DESCRIPTION OF THE INVENTION

According to the present invention, the base useful as a component of the catalyst can be an organic or an inorganic base, or combinations of two or more thereof. Suitable organic bases include, but are not limited to, trimethylamine, triethylamine, methylamine, ethylamine, dimethylamine, diethylamine, other amines, tetramethylammonium hydroxide, tetraethylammonium hydroxide, tetrapropylammonium hydroxide, tetramethylammonium bisulfide, tetraethylammonium bisulfide, and combinations of two or more thereof. Suitable inorganic bases include, but are not limited to, lithium hydroxide, sodium hydroxide, sodium hydrogensulfide, sodium sulfide, potassium hydroxide, potassium hydrogensulfide, calcium hydroxide, magnesium hydroxide, sodium bicarbonate, sodium carbonate, sodium oxide, magnesium oxide, calcium oxide, calcium carbonate, sodium phenoxide, barium phenoxide, calcium phenoxide, $R^1$ONa, $R^1$SNa, and combinations of two or more thereof; where $R^1$ is a $C_1$–$C_{18}$ alkyl radical. Presently, an inorganic base is preferred. Among the inorganic bases, sodium hydroxide is preferred because it is readily available and inexpensive.

According to the present invention, an aqueous medium denotes, unless otherwise indicated, a reaction medium, which does not contain substantial concentration of an organic solvent, for the contact of a polysulfide with a catalyst for the production of organic trisulfide. The term "substantial" means more than trivial. Generally, an aqueous medium can comprise regular tap water, deionized water, distilled water, a solution, a suspension, and combinations of two or more thereof. Presently it is preferred that regular tap water be used because it is readily available and economical. According to the present invention, any surfactant that facilitates the mixing of reactants into substantially a single phase can be used.

Generally, the surfactant comprises one or more compounds which exhibit surface-active properties. A preferred surfactant for use in the reaction system of the instant invention is selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of two or more thereof.

The presently preferred surfactant is an alkoxylated compound. Examples of suitable alkoxylated compounds include, but are not limited to, alkoxylated alcohols, alkoxylated mercaptans, sulfates of alkoxylated alcohols, alkoxylated phenols, sulfates of alkoxylated phenols, and combinations of two or more thereof.

The alkoxylated alcohol useful in the present invention has a general formula of $R^2O[CH_2CH(R^3)O]_qH$ where $R^2$ is a $C_1$–$C_{20}$ hydrocarbyl radical selected from the group consisting of alkyl radical, alkylaryl radical, aryl radical, cycloalkyl radical, alkenyl radical, and combinations of two or more thereof; Preferably $R^2$ is a $C_6$–$C_{18}$ alkyl radical. Most preferably $R^2$ is a $C_{10}$–$C_{16}$ alkyl radical; $R^3$ is selected from the group consisting of hydrogen, $C_1$–$C_{16}$ alkyl radicals, $C_2$–$C_{16}$ alkenyl radicals, and combinations of two or more thereof; and q is a number of from 1 to about 20, preferably from about 2 to about 12, most preferably from 5 to 10. Generally $R^3$ can contain from 0 to about 16 carbon atoms. Preferably $R^3$ is a hydrogen or a $C_1$–$C_3$ alkyl radical. Most preferably $R^3$ is hydrogen. An example of suitable alkoxylated alcohol is TERGITOL® 15-S-7 which is an ethoxylated alcohol, is manufactured and marketed by Union Carbide Corporation, and has the formula of $R^2O(CH_2CH_2O)_7H$ where $R^2$ is a secondary alkyl radical having 11–15 carbon atoms and 7 is the averaged number of the ethylene oxide units. Another example is an ethoxylated phenol having the same number of ethylene oxide units. Other suitable alkoxylated alcohols are also available from Union Carbide Corporation.

The sulfate of alkoxylated alcohol useful in the present invention has a general formula of $R^2O[CH_2CH(R^3)O]_q SO_3M$ where $R^2$, $R^3$, and q are the same as those described above and M is an alkali metal or an alkaline earth metal or combinations of two or more thereof. An example of suitable sulfate of alkoxylated alcohol is sodium sulfate of an ethoxylated alcohol having the formula of $R^2O(CH_2CH_2O)_q SO_3$ Na in which $R^2$ and q are the same as those disclosed above.

Useful alkoxylated phenols and sulfates of alkoxylated phenols can have general formulas of $(^3)_pArO[CH_2CH(R^3)O]_qH$ and $(R^2)_pArO[CH_2CH(R^3)O]_q SO_3M$, respectively where $R^2$, $R^3$, q and M are the same as those disclosed above, Ar is an aryl group, preferably a phenyl group, and p is an integer ranging from 0 to 5. Examples of these alkoxylated phenols are ethoxylated phenol ArO(CH$_2$CH$_2$O)$_q$H and sodium sulfate of ethoxylated phenol ArO(CH$_2$CH$_2$O)$_q$SO$_3$Na where Ar and q are the same as disclosed above.

The alkoxylated mercaptan useful in the present invention has a general formula of R$^2$S[CH$_2$CH(R$^3$)O]$_q$H where R$^2$, R$^3$, and q are the same as those described above. An example of an alkoxylated mercaptan is an ethoxylated mercaptan having the formula of R$^2$S(CH$_2$CH$_2$O)$_7$H where R$^2$ is primarily a tertiary dodecyl group and 7 is the averaged number of ethylene oxide units. This ethoxylated mercaptan is a surfactant, available under the trade name AQUA-CLEEN® II. Another example is an ethoxylated thiophenol having the same number of ethylene oxide units. Other suitable alkoxylated mercaptans are also available from Phillips Petroleum Company.

Quaternary ammonium salt useful in the present invention has the general formula (R$^4$)$_4$N$^+$X$^-$ where R$^4$ is an alkyl radical of from 1 to 20 carbon atoms; and X is selected from the group consisting of Br$^-$, Cl$^-$, I$^-$, F$^-$, R$^4$CO$_2^-$, QSO$_3^-$, BF$_4^-$, and HSO$_4^-$, where Q is an aryl, alkaryl or arylalkyl radical of 6 to 10 carbon atoms. It will be noted that a variety of anions are suitable as the component of the quaternary ammonium salts.

Useful quaternary ammonium salts according to the general formula given above include, but are not limited to, methyltrialkyl(C$_8$–C$_{10}$)ammonium chloride (also known as Adogen> 464), cetyltrimethylammonium bromide, hexadecyltrimethylammonium bromide, tetraheptylammonium bromide, cetyltrimethylammonium stearate, benzyltributylammonium chloride, benzyltriethylammonium bromide, benzyltrimethylammonium bromide, phenyltrimethylammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutyl ammonium fluoride, tetrabutylammonium tetrafluoroborate, and combinations of two or more thereof.

An alkali metal alkyl sulfate of the general formula of R$^4$OSO$_3$M can be used in the present invention, wherein R$^4$ and M are the same as those disclosed above. Examples of suitable compounds according to the general formula for the alkali metal alkyl sulfates include, but are not limited to, lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate, and combinations of two or more thereof.

Useful alkali metal salts of alkanoic acids have the general formula of R$^4$CO$_2$M, where R$^4$ and M have the same meaning as given above. Examples of suitable alkali metal salts of alkanoic acids include, but are not limited to, lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosanoate, potassium eicosanoate, and combinations of two or more thereof.

Useful alkali metal salts of alkaryl sulfonic acids have the general formula of (R$^4$)$_p$ArSO$_3$M where R$^4$ and M are the same as those disclosed above, Ar is an aryl group or a phenyl group, and p is an integer ranging from 0 to 5.

Typical compounds within the group include, but are not limited to, sodium dodecylbenzenesulfonate, potassium dodecylbenzenesulfonate, lithium dodecylbenzenesulfonte, sodium tetradecylbenzenesulfonate, potassium hexadecylbenzenesulfonate, rubidium dodecylbenzenesulfonate, cesium dodecylbenzenesulfonate, sodium octadecylbenzenesulfonte, potassium octadecylbenzenesulfonate, sodium eicosylbenzenesulfonate, and combinations of two or more thereof.

Examples of suitable 1-alkyl pyridinium salts include, but are not limited to, 1-dodecylpyridinium paratoluenesulfonate, 1-dodecylpyridinium chloride, 1-hexadecylpyridinium chloride, 1-hexadecylpyridinium paratoluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and combinations of two or more thereof.

The weight ratio of surfactant to base can vary widely, preferably from about 0.001:1 to about 1000:1, more preferably about 0.01:1 to about 100:1, and most preferably from about 0.1:1 to 50:1 for best results.

The catalyst can be made by properly mixing the base and surfactant in the ratio described above employing any suitable mixing means such as shaking or stirring. Presently, it is preferred that the catalyst be produced in-situ by adding a base and a surfactant to a reaction vessel or reactor that is used for producing a trisulfide.

The organic polysulfide compound that can be used as a starting reactant has a general formula of RS$_n$R in which each R can be the same or different hydrocarbyl radical having 1 to about 20 carbon atoms selected from the group consisting of alkyl, aryl, cycloalkyl, alkylaryl, and alkenyl radicals. Preferably each R is an alkyl radical having 3 to 15 carbon atoms. Most preferably each R is the same and is each a tertiary alkyl radical. The n is about 4 or greater.

The organic trisulfide can be produced by the reaction of mercaptans and the organic polysulfide catalyzed by the catalyst disclosed above. The reaction is depicted as n$^1$RSH+n$^2$RS$_n$R→n$^3$RSSSR+n$^4$H$_2$S where R and n are the same as those described above and n$^1$, n$^2$, n$^3$, and n$^4$ are dependent on n. For example, if n=4, then n$^1$=2, n$^2$=2, n$^3$=3, and n$^4$=1; if n=5, then n$^1$=2, n$^2$=1, n$^3$=2, and n$^4$=1. The reaction can be carried out in any suitable reaction vessel. The choice of reaction vessel is a matter of preference to those skilled in the art.

The catalyst also can be formed in-situ by adding a base and a surfactant before or during the contacting of a mercaptan and the organic polysulfide.

The suitable conditions for the contacting of mercaptan with an organic polysulfide can include a temperature in the range of from about 20° C. to about 250° C., preferably from 50° C. to 150° C. and a time of from about 10 minutes to about 10 hours, preferably 30 minutes to 5 hours. The pressure can vary widely from about 1 atmosphere to about 30 atmospheres, preferably from about 1 atmosphere to about 10 atmospheres.

Generally, one of the reactants, either the mercaptan or organic polysulfide, is added to the other reactant in the presence of the catalyst described above to form a reaction mixture. The molar amount of mercaptan and the molar amount of polysulfide molecule are shown in the above equation. For example, 2 moles of mercaptan and 1 mole of organic pentasulfide are reacted to produce 2 moles of trisulfide and 1 mole of H$_2$S. The weight of the catalyst (base and surfactant) as a percentage of the weight of mercaptan is generally in the range of from 0.01 to 50%, preferably about 0.05 to 20%, and most preferably 0.1 to 10%.

During the reaction, residual hydrogen sulfide is generally removed or allowed to escape from reaction mixture or reaction vessel which the crude organic trisulfide product contains, for example, continuously or periodically venting off $H_2S$. Any unreacted mercaptan is generally removed by any means known to one skilled in the art such as, for example, distillation. The trisulfide product can also be further purified and/or stabilized, if necessary, by means known to one skilled in the art such as the methods disclosed in U.S. Pat. Nos. 5,155,147; 5,206,439; and 5,218,147, disclosures of which are herein incorporated by reference. For example, a crude trisulfide product can be contacted with an acid or an alkylene oxide to further stabilize the polysulfide. Optionally, one of the bases described above can also be added to the alkylene oxide as a catalyst. The alkylene oxide can have 1 to about 10 carbon atoms. The presently preferred alkylene oxide has 1 to 4 carbon atoms and is selected from the group consisting of ethylene oxide, propylene oxide, 1,2-butylene oxide, isobutylene oxide, and mixtures thereof.

Any acid can be used to purify the organic trisulfide product. Examples of suitable acids include, but are not limited to, sulfuric acid, nitric acid, hydrochloric acid, phosphoric acid, formic acid, trifluoroacetic acid, trichloroacetic acid, methanesulfonic acid, partially or fully neutralized acids wherein one or more protons have been replaced with, for example, a metal ion such as an alkali metal ion or ammonium ion, and combinations of two or more thereof. Examples of partially or fully neutralized acids include, but are not limited to, sodium bisulfate, ammonium sulfate, ammonium chloride, ammonium nitrate, and combinations of two or more thereof. The presently preferred acid is sulfuric acid which is readily available.

A solvent also optionally can be used in the alkylene oxide treatment of polysulfides. The solvent generally is substantially miscible with the basic catalyst employed. It can be an ether, an alcohol or water. Suitable solvents include methanol, ethanol, propanol, tetrahydrofuran, water, and other similar oxygen-containing solvents. Methanol is the presently preferred solvent because of its combined solubilization properties, high vapor pressure, and lower density thus providing a greater density contrast between the alcohol-phase and the polysulfide phase, thereby simplifying the phase separation.

The molar ratio of the alkylene oxide to the organic trisulfide can be from about 0.001:1 to about 50:1, preferably from about 0.005:1 to about 2:1, and most preferably from 0.01:1 to 1:1. The molar ratio of the basic catalyst, if present, to the organic trisulfide can range from about 0.001:1 to about 2:1, preferably from about 0.005:1 to about 1:1, and most preferably from 0.01:1 to 0.1:1. The molar ratio of the solvent, if employed, to the organic trisulfide can be from about 0.001:1 to about 20:1, preferably from about 0.01:1 to about 10:1, and most preferably from 0.02:1 to 1:1.

Though the basic catalyst is generally added to the crude organic trisulfide first, the order of adding the alkylene oxide and basic catalyst generally does not significantly affect the purity and stability of the final product. Generally, following the addition of the basic catalyst to the crude organic trisulfide, the mixture is mixed by a suitable means such as stirring and can be heated to about 50–150° C., preferably about 60–100° C., most preferably 65–80° C., followed by the addition of alkylene oxide. The heating step can also be carried out after the alkylene oxide is added to the mixture.

The mixture is then further heated at the same temperature range described above for about 10 minutes to about 10 hours, preferably about 30 minutes to about 5 hours, most preferably 1 hour to 3 hours. Upon completion of heating, nitrogen sparge into the mixture can be initiated at about 1 to about 10 standard cubic feet per hour for about 10 minutes to about 5 hours.

The heated mixture can be further purified if necessary. This is usually done by conventional separation means such as filtration to remove any impurities or by distillation.

The process of the invention can also be carried out continuously. For example, the contacting of mercaptans with organic polysulfide in the presence of the catalyst can be done by employing continuous stir tank reactors connected in series, packed columns or towers in which the invention catalyst is supported on a solid support, and other continuous flows that are readily within the realm of one skilled in the art.

The following examples are provided to further illustrate the practice of the invention and are not intended to limit the scope of the invention of the claims.

EXAMPLE I

This example illustrates the production of the catalyst which can be used in the invention.

To a 200 ml flask equipped with thermowell, magnetic stirring bar, and condenser with $N_2$ inlet on top, was added 97.0 g of ethoxylated alcohol (Union Carbide TERGITOL® 15-5-7) and 3.0 g of NaOH pellets. The mixture under $N_2$ was heated at 80° C. with stirring for 1 hour. The liquid was clear and reddish orange after heating. After cooling, the flask was stoppered. Avoid exposure to air as much as possible.

The catalyst was also prepared the same way as described above except that 97.0 g of the ethoxylated alcohol and 6.0 g of 50% aqueous NaOH were used.

EXAMPLE II

This example illustrates the preparation of di-t-butyl trisulfide using catalyst made in-situ in the reaction vessel from an ethoxylated alcohol and sodium hydroxide.

To a 250 ml, 3-necked flask equipped with thermowell, magnetic stirring bar, pressure equalizing addition funnel, and condenser with both line to flare on top and $N_2$ inlet, was added 0.080 g of 50% aqueous NaOH, 0.48 g of Tergitol 15-S-7 and 33 g of di-t-butyl polysulfide containing average of 4.4 sulfur atoms per molecule. The reaction vessel was purged with $N_2$. In the addition funnel was placed 47 g of t-butyl mercaptan. Then about ⅓ of the mercaptan was added to the flask so that stirring and heating could be started. The reaction mixture was heated to 60° C.; and the rest of the mercaptan was added in portions while the temperature was raised to 60° C. The reaction mixture was then heated at 60° C. for 1 hour. GC analysis of the reaction mixture at this time showed that it consisted of 69.9% di-t-butyl trisulfide, 4.1% tetrasulfide, 1.5% disulfide, and 24.2% t-butyl mercaptan. Without the mercaptan this would mean 92.2% trisulfide, 5.4% tetrasulfide, and 1.9% disulfide which is essentially the same mixture obtained from t-butyl mercaptan and sulfur in U.S. Pat. No. 5,530,163. At this point the reaction mixture was cooled, neutralized with aqueous sulfuric acid, and then excess mercaptan removed as in U.S. Pat. No. 5,530,163 with essentially no changes in the percentage of trisulfide, tetrasulfide, and disulfide given above. The yield was 100%.

EXAMPLE III

This example shows the preparation of di-t-butyl trisulfide by preparation of di-t-butyl polysulfide (average 4.4 S per molecule) first followed by converting it to the trisulfide.

To a 500 ml 3-necked flask equipped as in the above procedure was added 33.7 g of sulfur, 0.96 g of Tergitol 15-S-7, and 0.17 g of 50% aqueous NaOH. The setup was purged with $N_2$. To the addition funnel was added 55.7 g of t-butyl mercaptan. About ¼ of the mercaptan was added so stirring and heating could be started. The flask was heated to 50° C. The rest of the mercaptan was added in portions while heating over 20 minutes to and at 50° C. Hydrogen sulfide was evolved during the addition of mercaptan. After all the mercaptan was added, the reaction mixture was heated at 60° C. for 1 hour. GC analysis at this time showed that the reaction mixture consisted of 38.3% di-t-butyl trisulfide, 44.8% tetrasulfide, 15.4% penta, 0.3% disulfide, and 1.1% t-butyl mercaptan. Without the mercaptan this would mean 38.7% trisulfide, 45.3% tetrasulfide, 15.6% pentasulfide, and 0.3% disulfide. This is typical of a polysulfide with an average of 4.4 sulfurs.

At this point, 89.1 g of additional t-butyl mercaptan was added from the addition funnel in portions at 60° C. over 15 minutes. After stirring at 60° C. for an additional 1.25 hours, GC analysis of the reaction mixture showed that it consisted of 66.6% di-t-butyl trisulfide, 4.0% tetrasulfide, 1.4% disulfide and 27.8% t-butyl mercaptan. Without the mercaptan this would mean 92.3% trisulfide, 5.5% tetrasulfide, and 1.9% disulfide which is typical of that produced in one step from mercaptan and sulfur in U.S. Pat. No. 5,530,163. At this point the reaction mixture was cooled and 0.35 g of aqueous sulfuric acid solution (made from 2 parts by weight water and 1 part concentrated $H_2SO_4$) was added with stirring. The experiment was completed as in U.S. Pat. No. 5,530,163 to remove excess mercaptan. There was essentially no change in the percentages of trisulfide, tetrasulfide, or disulfide from those reported above. The yield was essentially 100%.

EXAMPLE IV

Di-t-butyl polysulfide containing average of 4.4 sulfur atoms per molecule (99 g), 79 g of t-butyl mercaptan, and 2.5 mls of triethylamine were mixed and heated in an autoclave at 130° C. for 6 hours (pressure as 60–70 psig at 130° C.). Hydrogen sulfide which was formed was periodically vented from the reactor during the run. The product, excluding excess mercaptan and triethylamine, contained 83.9% trisulfide, 14.9% tetrasulfide, and 1.2% disulfide. Further heating did not reduce the tetrasulfide any more.

Excess t-butyl mercaptan was removed from the crude reactor product by distillation under reduced pressure as in the previous examples. After excess t-butyl mercaptan was removed, the trisulfide was distilled (63–70 ° C. heat temperature at 2 torr) to remove it from the tetrasulfide. The distilled di-t-butyl trisulfide contained greater than 98% trisulfide.

Example IV shows that triethylamine can convert polysulfide to trisulfide, but the combination of NaOH and a surfactant is a more effective catalyst system since it did it at a lower temperature and caused the final tetrasulfide concentration to be lower.

The results shown in the above examples clearly demonstrate that the present invention is well adapted to carry out the objects and attain the ends and advantages mentioned was well as those inherent therein. While modifications may be made by those skilled in the art, such modifications are encompassed within the spirit of the present invention as defined by the disclosure and the claims.

That which is claimed is:

1. A process for producing an organic trisulfide comprising contacting a mercaptan with an organic polysulfide in the presence of a catalyst wherein said polysulfide has more than 3 sulfur atoms per molecule and said catalyst comprises a base and further comprises a surfactant selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of two or more thereof.

2. A process according to claim 1 wherein said base is selected from the group consisting of triethylamine, trimethylamine, tetramethylammonium hydroxide, tetraethylammonium hydroxide, tetrapropylammonium hydroxide, tetramethylammonium bisulfide, tetraethylammonium bisulfide, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, potassium carbonate, sodium phenoxide, barium phenoxide, calcium phenoxide, NaSH, $Na_2S$, $R^1ONa$, $R^1SNa$, and combinations of two or more 10 thereof wherein $R^1$ is a $C_1$–$C_{18}$ alkyl radical.

3. A process according to claim 1 wherein said base is sodium hydroxide.

4. A process according to claim 1 wherein said surfactant is selected from the group consisting of alkoxylated mercaptans, alkoxylated alcohols, and combinations of any two or more thereof.

5. A process according to claim 1 wherein said surfactant is an alkoxylated alcohol.

6. A process according to claim 5 wherein said alkoxylated alcohol has a general formula of $R^2O[CH_2CH(R^3)O]_qH$ wherein $R^2$ is a hydrocarbyl radical selected from the group consisting of alkyl radical, alkylaryl radical, aryl radical, cycloalkyl radical, alkenyl radical and combinations of two or more thereof; $R^3$ is selected from the group consisting of hydrogen, $C_1$–$C_{16}$ alkyl radical, $C_2$–$C_{16}$ alkenyl radical and combinations of two or more thereof; and q is a number of from 1 to about 20.

7. A process according to claim 5 wherein said alkoxylated alcohol the formula of $R^2O(CH_2CH_2O)_7H$, wherein $R^2$ is a secondary alkyl radical having 11 to 15 carbon atoms.

8. A process according to claim 7 wherein said base is sodium hydroxide.

9. A process according to claim 1 wherein said base is triethylamine.

10. A process according to claim 1 wherein said surfactant is a quaternary ammonium salt.

11. A process according to claim 1 wherein said surfactant is methyltrialkyl($C_8$–$C_{10}$)ammonium chloride.

12. A process according to claim 1 wherein said organic trisulfide is t-butyl trisulfide.

13. A process according to claim 8 wherein said organic trisulfide is t-buty-1 trisulfide.

14. A process for producing an organic trisulfide comprising contacting a mercaptan with an organic polysulfide in the presence of a catalyst wherein said polysulfide has about 4 or more sulfur atoms per molecule and said catalyst comprises a base and a surfactant;

said base is selected from the group consisting of tetramethylammonium hydroxide, trimethylamine, triethylamine, tetraethylammonium hydroxide,, tetrapropylammonium hydroxide, tetramethylammonium bisulfide, tetraethylammonium bisulfide, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, potassium carbonate, sodium phenoxide, barium phenoxide, calcium phenoxide, NaSH, $Na_2S$, $R^1ONa$, $R^1SNa$, and combinations of two or more thereof wherein $R^1$ is a $C_1$–$C_{18}$ alkyl radical; and said surfactant is selected from the group consisting of alkoxylated compounds, quaternary ammonium salts, alkali metal alkyl sulfates, alkali metal salts of alkanoic acids, alkali metal salts of alkaryl sulfonic acids, 1-alkyl pyridinium salts, and combinations of two or more thereof.

15. A process according to claim 14 wherein said surfactant is an alkoxylated alcohol; and said base is sodium hydroxide.

16. A process according to claim 15 wherein said alkoxylated alcohol the formula of $R^2O(CH_2CH_2O)_7H$, wherein $R^2$ is a secondary alkyl radical having 11 to 15 carbon atoms.

17. A process for producing a stable di-t-butyl trisulfide comprising: (1) contacting t-butyl mercaptan with di-t-butyl polysulfide in the presence of a catalyst at a temperature in the range of from 50° C. to 150° C. for 30 minutes to 5 hours to form a product mixture; wherein said catalyst is prepared by heating sodium hydroxide and an ethoxylated alcohol having the formula of $R^2O(CH_2CH_2O)_7H$ wherein $R^2$ is a secondary alkyl radical having 11–15 carbon atoms; and (2) contacting said product mixture with an aqueous acid solution.

18. A process according to claim 17 wherein said catalyst is triethylamine.

19. A process according to claim 17 wherein said acid is sulfuric acid.

* * * * *